United States Patent
Tyree

[11] 4,027,528
[45] June 7, 1977

[54] APPARATUS FOR ULTRASONIC INSPECTION OF FERROMAGNETIC MATERIALS

[76] Inventor: Bill D. Tyree, 3997 Bellwood Court, Concord, Calif. 94520

[22] Filed: Dec. 15, 1975

[21] Appl. No.: 640,726

[52] U.S. Cl. ............................................. 73/67.8 S
[51] Int. Cl.² ........................................ G01N 29/04
[58] Field of Search .............. 73/67.5 R, 67.6, 67.7, 73/67.8 R, 67.8 S, 67.9, 71.5 VS; 324/37 R; 250/360; 180/1 US

[56] References Cited
UNITED STATES PATENTS

| | | | |
|---|---|---|---|
| 2,666,862 | 1/1954 | Branson | 73/71.5 US X |
| 3,810,515 | 5/1974 | Ingro | 180/1 VS |
| 3,844,164 | 10/1974 | Romere | 73/71.5 US X |

FOREIGN PATENTS OR APPLICATIONS 739,998   11/1955   United Kingdom .......... 73/71.5 US

*Primary Examiner*—Richard C. Queisser
*Assistant Examiner*—John P. Beauchamp

[57] ABSTRACT

Apparatus for use in inspecting ferromagnetic wall members. The apparatus comprises a telescopically extendable pole member having a carriage attached to the extendable end of the telescope. The carriage comprises a mounting frame attached to one of its ends to the extendable end of the telescope. A shaft extends through the mid portion of the mounting frame generally perpendicular to the telescope. Wheels consisting at least in part of permanent magnetic material are rotatably mounted on each end of the shaft. An ultrasonic transducer is attached to the other end of the mounting frame. An electric current carrying cable is electrically connected to the transducer and a waterline having an open end adjacent the end of the transducer is attached to the mounting frame.

1 Claim, 3 Drawing Figures

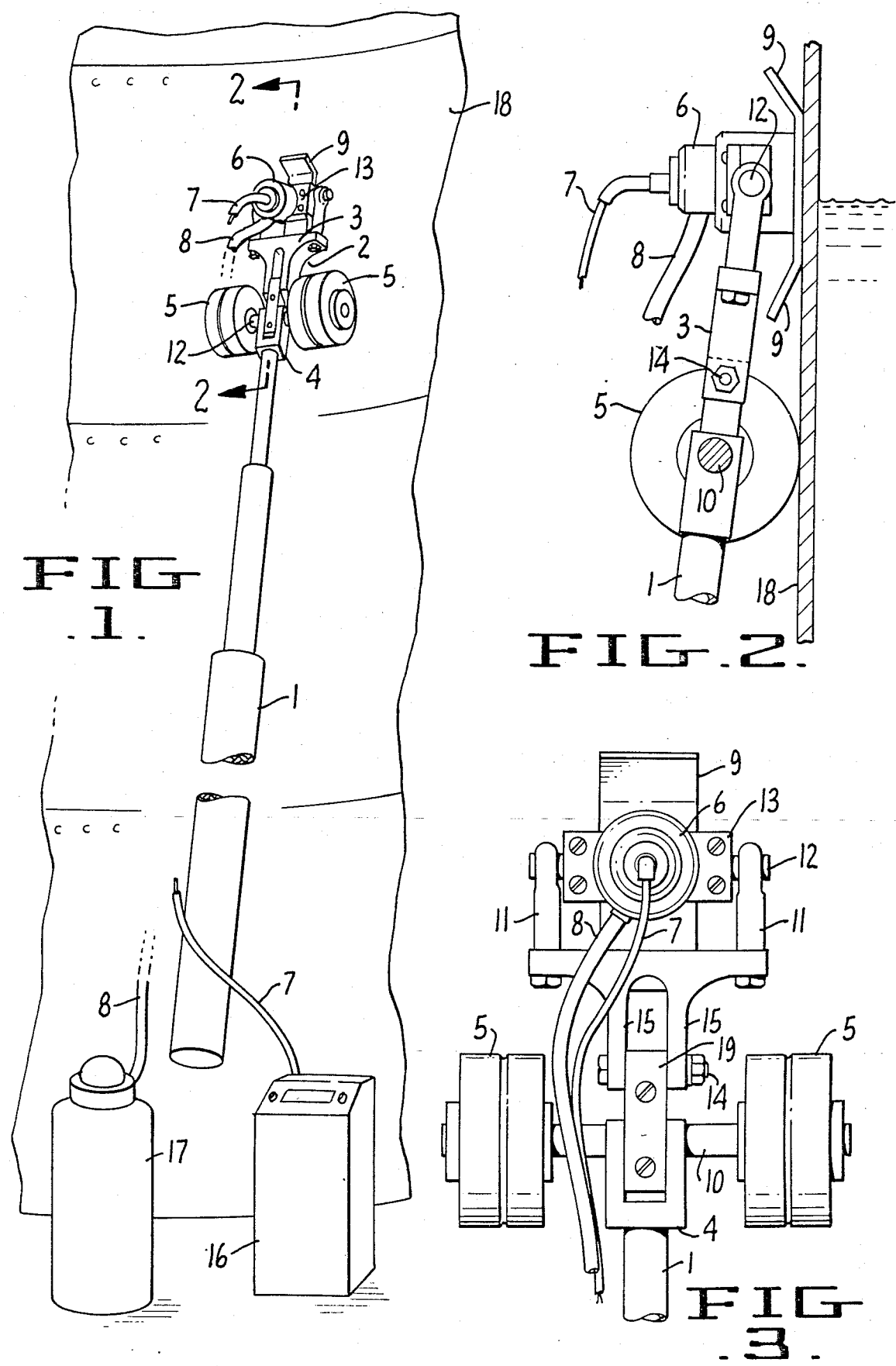

APPARATUS FOR ULTRASONIC INSPECTION OF FERROMAGNETIC MATERIALS

BACKGROUND OF THE INVENTION

In the past there has been considerable study of the use of ultrasound in non-destructive testing and inspection of metals. Ultrasonic metal inspection is described in McGraw-Hill *Encyclopedia of Science and Technology* (1971) in volume 8 at page 340. Specific applications of ultrasound to metal inspection are described in U.S. Pat. Nos. 3,844,164 and 3,850,028.

Ultrasonic inspection apparatus heretofore available has not been well adapted for use in inspection of existing, in-use metal walls which have an extended vertical dimension such as oil refinery tanks, reaction vessels, distillation columns, steel ship hulls, and the like. Oil tanks, for example, are commonly inspected by attaching an ultrasonic transducer to a line. An operator positions himself on the top of the tank and using a winch pulls in the line, thus raising the ultrasonic transducer from ground level to the top of the tank, hopefully keeping reasonably good contact between the transducer and the tank wall surface as it rises. The ultrasonic transducer is then lowered to the ground, moved laterally and again raised to the top of the tank by the line and this procedure is repeated working around the circumference of the tank.

The present invention provides apparatus capable of making rapid and efficient inspection of vertical metal walls which are formed of a ferromagnetic material such as iron, steel and the like.

SUMMARY OF THE INVENTION

The apparatus of the present invention is comprised of a telescopic pole member and a carriage. The carriage comprises a mounting frame, one end of which is attached to the movable end of the telescopic pole member. An ultrasonic transducer is mounted on the other end of the mounting frame. A shaft extends through the central portion of the mounting frame and is so arranged that it is generally perpendicular to the pole member. Wheels formed at least in part of a permanent magnetic material are rotatably attached to each end of the shaft. An electrically conductive cable is connected to the transducer to carry the electric current required to energize the transducer. A waterline is attached to the mounting frame and is so arranged that it has an open end adjacent the emitting face of the transducer and this line carries water from a reservoir to the space between the emitting surface of the transducer and the workpiece where it serves as a coupling liquid.

In inspection of vertical ferromagnetic structure, the apparatus is operated from the ground. The magnetic wheels are placed in contact with the surface of the structure, thus bringing the emitting surface of the transducer into close contact with the structure surface. The transducer is energized and water is forced through the waterline to function as a coupling liquid and then the telescopic pole member is extended either manually or hydraulically causing the magnetic wheels to roll up the face of the vertical structure so that the transducer traverses a generally vertical path to the top of the structure. This operation is repeated so that a series of vertical traverses are made which cover the entire surface of the vertical wall at closely spaced intervals. The strength of the permanently magnetic material of the wheels is such that the carriage is firmly held against the surface of the ferromagnetic structure by magnetic attraction. The carriage weight is generally in the range 3 to 4 pounds and in the event that the carriage is displaced from the surface of the structure in any manner the carriage, being firmly attached to the telescopic pole member, is prevented from falling.

DETAILED DESCRIPTION OF THE INVENTION

Details of the inspection apparatus are shown in the appended drawings of which FIG. 1 is a semi-plan view of the apparatus ready for operation.

FIG. 2 is a cross section of the carriage along line 2—2 of FIG. 1.

FIG. 3 is a plan view of the carriage. Referring now to FIG. 1, telescopic pole member 1 is a telescopically extendable pole. Suitable poles for this purpose are manufactured by Hastings Fibreglass Products, Inc., Hastings, Mich. The base of the pole member is at or near ground level and indeed its lower end may be rested on the ground.

Carriage assembly 2 is attached to the extendable end of the pole member.

Carriage member 2 consists of mounting frame 3 which is attached to pole member 1 at attachment junction 4. Two magnetic wheels 5 are rotatably mounted on shaft 10 which extends through the mounting frame and is perpendicular to pole member 1. Ultrasonic transducer 6 is held by support 13 at the upper end of the mounting frame. Fender 9 is located at the extreme upper end of the mounting frame and serves to keep the emitting head of the transducer generally parallel to the surface of the workpiece, i.e., tank 18 shown in break away in the drawing. Wire line 7 extends from the power supply recorder station 16. Waterline 8 extends from water pressure vessel 17 to the upper end of the mounting frame and passes through the frame so that its open end is adjacent the emitting face of transducer 6.

FIG. 2 is a cross-sectional view of the carriage showing the position of the several elements of the carriage referred to in the discussion of FIG. 1 as they appear in cross-section.

FIG. 3 of the drawings is a plan view of the carriage showing its construction in greater detail. Transducer support member 13 is mounted on shaft 12 which extends between the two arms 11 which extend from the upper end of the mounting frame assembly. This arrangement permits moderate rocking action of the transducer as it passes over rough portions of the surface of the workpiece. Arms 15 of the mounting frame assembly extend downward and are rotatably mounted on shaft 14 which passes through deep plate member 19 of the mounting frame assembly and this mounting also permits some rocking action of the transducer support. Magnetic wheels 5 are three to four inches in diameter and comprise strongly permanent magnetic material which permits the wheels to hold fast to the surface of tank 18 by magnetic attraction.

Extension or retraction of telescopic pole member 1 causes the transducer to move vertically upward or downward over the tank surface. Ultrasonic waves are reflected from the interior surface of the metal sheet constituting the tank wall. The reflected waves cause variations in the current movement in line 7 which are detected by power-recorder package 16. Corroded areas of the tank wall surface are thinner than the uncorroded areas and the ultrasonic waves are reflected more quickly from these areas and the response variation is noted at the recorder.

A prototype of the apparatus of the invention was built and used in the inspection of some thirty oil storage tanks located in a large West Coast refinery. The tanks ranged from 30 to 45 feet in height and 40 to 60 feet in diameter. The inspection results were in all cases satisfactory.

In a representative operation an oil storage tank 60 feet in diameter and 45 feet in height was inspected by running the carriage vertically from bottom to top of the tank surface at 24 equally spaced intervals. A two-man team performed the inspection and completed it in just under eight hours. No significant deviations in wall thickness were detected. Had a deviation been detected then, the adjacent tank surface would have been further inspected by running the apparatus vertically up the tank surface at more closely spaced intervals.

What is claimed is:

1. Apparatus for non-destructive inspection of vertical ferromagnetic wall members comprising:
   A. a carriage, said carriage comprising
      1. a mounting frame having one pair of arms extending upwardly and a second pair of arms extending downwardly,
      2. a deep plate member fitted between the downwardly extending arms of the mounting frame and a shaft passing through said arms and said plate member,
      3. a shaft passing through the upwardly extending arms of the mounting frame and a support member mounted on said shaft in rocking engagement with said shaft,
      4. an ultrasonic transducer mounted on said support member,
      5. a fender member mounted on the lower surface of said support member,
      6. a shaft passing through said plate member and a wheel formed from strongly permanent magnetic material mounted on each end of said shaft,
   B. an electric current carrying cable in electric connection with said transducer,
   C. a waterline having an open end adjacent the face of the transducer, and
   D. a telescopic pole member supporting said carriage attached to the deep plate member and so aligned that it is perpendicular to the shaft on which the magnetic wheels are mounted.

* * * * *